(12) United States Patent
Hirano et al.

(10) Patent No.: US 11,666,228 B2
(45) Date of Patent: Jun. 6, 2023

(54) MEASURING APPARATUS, MEASURING METHOD, AND PROGRAM

(71) Applicant: KYOCERA Corporation, Kyoto (JP)

(72) Inventors: Asao Hirano, Tokyo (JP); Tomoyuki Tougasaki, Sagamihara (JP); Takeshi Higuchi, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 520 days.

(21) Appl. No.: 16/492,097

(22) PCT Filed: Feb. 19, 2018

(86) PCT No.: PCT/JP2018/005805
§ 371 (c)(1),
(2) Date: Sep. 6, 2019

(87) PCT Pub. No.: WO2018/163784
PCT Pub. Date: Sep. 13, 2018

(65) Prior Publication Data
US 2020/0297221 A1    Sep. 24, 2020

(30) Foreign Application Priority Data

Mar. 8, 2017 (JP) .............................. JP2017-044077
Aug. 24, 2017 (JP) .............................. JP2017-161545

(51) Int. Cl.
*A61B 5/0205* (2006.01)
*A61B 5/026* (2006.01)
(Continued)

(52) U.S. Cl.
CPC ........ *A61B 5/02055* (2013.01); *A61B 5/0261* (2013.01); *A61B 5/14552* (2013.01);
(Continued)

(58) Field of Classification Search
CPC .... A61B 2562/0233; A61B 2562/0238; A61B 2562/0271; A61B 5/02055;
(Continued)

(56) References Cited

U.S. PATENT DOCUMENTS 5,575,285 A    11/1996 Takanashi et al.
5,598,841 A    2/1997 Taniji et al.
(Continued)

FOREIGN PATENT DOCUMENTS

JP    H0321208 Y2    5/1991
JP    H06-066633 U   9/1994
(Continued)

OTHER PUBLICATIONS

Yasuma, Fumihiko "Periodic breathing with central sleep apnea at high altitude" Sleep Related Breathing Disorders. Nippon Rinsho, vol. 66, Suppl 2, 2008, pp. 245-248.

*Primary Examiner* — Jonathan T Kuo
(74) *Attorney, Agent, or Firm* — Studebaker & Brackett PC

(57) ABSTRACT

A measuring apparatus includes a first laser light source for emitting laser light of a first wavelength, a second laser light source for emitting laser light of a second wavelength different from the first wavelength, an optical detector for receiving scattered laser light from a measured part, and a controller configured to calculate a first value based on an output of the optical detector that is based on received scattered laser light of the first wavelength, calculate a second value based on an output of the optical detector that is based on received scattered laser light of the second wavelength, and measure oxygen saturation based on a ratio of the first value to the second value.

22 Claims, 8 Drawing Sheets

(51) Int. Cl.
   *A61B 5/1455*  (2006.01)
   *A61B 5/00*    (2006.01)
   *G01J 3/44*    (2006.01)
   *A61B 5/022*   (2006.01)

(52) U.S. Cl.
   CPC .......... *A61B 5/7275* (2013.01); *G01J 3/4412* (2013.01); *A61B 5/02233* (2013.01); *A61B 2562/0233* (2013.01); *A61B 2562/0271* (2013.01)

(58) Field of Classification Search
   CPC . A61B 5/02233; A61B 5/0261; A61B 5/0285; A61B 5/14552; A61B 5/7275; G01J 3/4412
   See application file for complete search history.

(56) References Cited

U.S. PATENT DOCUMENTS

| | | | |
|---|---|---|---|
| 6,785,568 B2* | 8/2004 | Chance | A61B 5/14551 600/340 |
| 9,314,197 B2* | 4/2016 | Eisen | A61B 5/14551 |
| 9,345,439 B2* | 5/2016 | Bechtel | A61B 5/1495 |
| 10,390,716 B2* | 8/2019 | Shimuta | A61B 5/02438 |
| 2002/0161290 A1* | 10/2002 | Chance | A61B 5/1459 600/323 |
| 2007/0088228 A1 | 4/2007 | Uchida et al. | |
| 2008/0171915 A1 | 7/2008 | Kawajiri et al. | |
| 2008/0208019 A1 | 8/2008 | Nitzan | |
| 2010/0056887 A1 | 3/2010 | Kimura et al. | |
| 2010/0240973 A1* | 9/2010 | Presura | A61B 5/14551 600/335 |
| 2013/0317331 A1* | 11/2013 | Bechtel | A61B 5/7405 600/328 |
| 2014/0200423 A1* | 7/2014 | Eisen | A61B 5/7278 600/340 |
| 2017/0027459 A1* | 2/2017 | Shimuta | A61B 5/02438 |
| 2017/0095168 A1* | 4/2017 | Kwon | A61B 5/02427 |
| 2017/0251962 A1* | 9/2017 | Shiho | A61B 5/681 |
| 2017/0273575 A1* | 9/2017 | Umekawa | A61B 5/7278 |
| 2020/0029875 A1* | 1/2020 | Hirano | A61B 5/0261 |

FOREIGN PATENT DOCUMENTS

| | | |
|---|---|---|
| JP | H07-92184 A | 4/1995 |
| JP | H07-171140 A | 7/1995 |
| JP | 2006247133 A | 9/2006 |
| JP | 2007105323 A | 4/2007 |
| WO | 95/12349 A1 | 5/1995 |
| WO | 2008065699 A1 | 6/2008 |

* cited by examiner

MEASURING APPARATUS, MEASURING METHOD, AND PROGRAM

CROSS-REFERENCE TO RELATED APPLICATION

This application claims priority to and the benefit of Japanese Patent Applications No. 2017-044077 (filed on Mar. 8, 2017) and No. 2017-161545 (filed on Aug. 24, 2017), the entire contents of which are incorporated herein by reference.

TECHNICAL FIELD

The present disclosure relates to a measuring apparatus, a measuring method, and a program.

BACKGROUND

Pulse oximeters for measuring arterial oxygen saturation are conventionally known (e.g., see PTL 1). Blood flow measuring apparatus that emit laser light to a fingertip and measure blood flow based on scattered light from the blood flow in fingertip capillaries are conventionally known (e.g., see PTL 2).

SUMMARY

A measuring apparatus according to an embodiment includes a first laser light source, a second laser light source, an optical detector, and a controller. The first laser light source emits laser light of a first wavelength. The second laser light source emits laser light of a second wavelength different from the first wavelength. The optical detector receives scattered laser light from a measured part. The controller is configured to calculate a first value based on an output of the optical detector that is based on received scattered laser light of the first wavelength, calculate a second value based on an output of the optical detector that is based on received scattered laser light of the second wavelength, and measure oxygen saturation based on a ratio of the first value to the second value.

A measuring method according to an embodiment is a measuring method of a measuring apparatus. The measuring method includes a step of emitting laser light of a first wavelength to a measured part, a step of emitting laser light of a second wavelength different from the first wavelength to the measured part, and a step of receiving scattered laser light from the measured part. The measuring method also includes a step of calculating a first value based on the received scattered laser light of the first wavelength, a step of calculating a second value based on the received scattered laser light of the second wavelength, and a step of measuring oxygen saturation based on a ratio of the first value to the second value.

A program according to an embodiment causes a computer to execute a step of emitting laser light of a first wavelength to a measured part, a step of emitting laser light of a second wavelength different from the first wavelength to the measured part, and a step of receiving scattered laser light from the measured part. The program also causes the computer to execute a step of calculating a first value based on received scattered laser light of the first wavelength, a step of calculating a second value based on received scattered laser light of the second wavelength, and a step of measuring oxygen saturation based on a ratio of the first value to the second value.

DETAILED DESCRIPTION

Hereinafter, embodiments of the present disclosure will be described in detail with reference to the accompanying drawings.

First Embodiment

Figure 1:
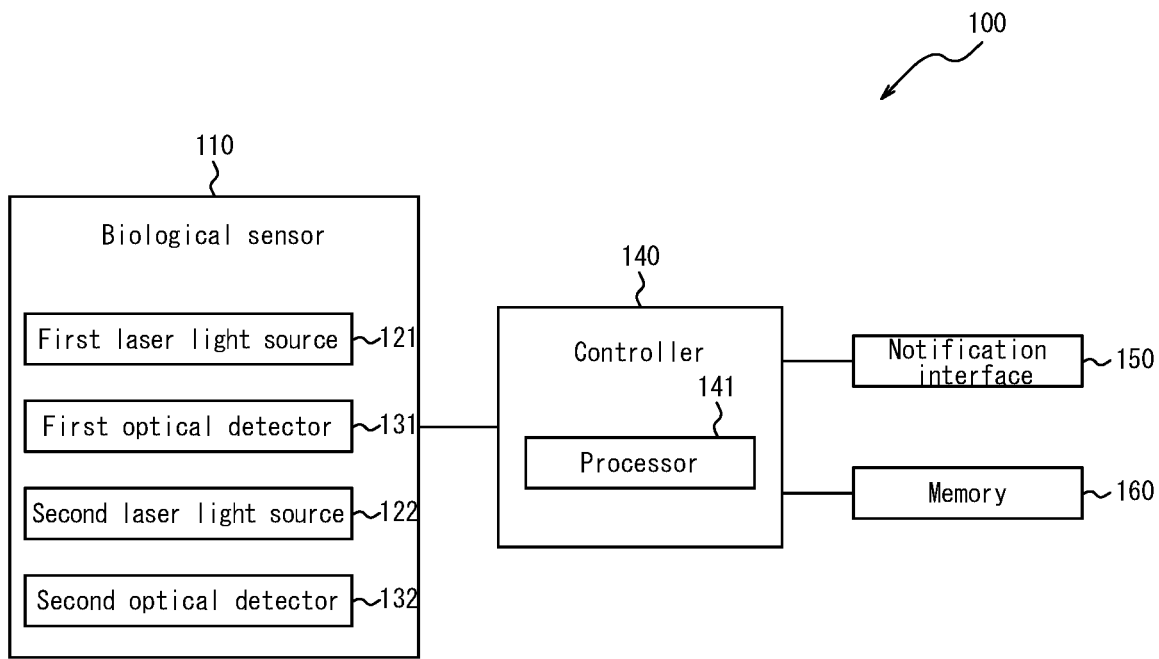
FIG. 1 is a functional block diagram illustrating a schematic configuration of a measuring apparatus according to a first embodiment.

FIG. 1 is a functional block diagram illustrating a schematic configuration of a measuring apparatus 100 according to a first embodiment. The measuring apparatus 100 according to the present embodiment includes a biological sensor 110, a controller 140, a notification interface 150, and a memory 160.

The measuring apparatus 100 acquires a biological measurement output of a subject (a user) in contact with the measuring apparatus 100 by using the biological sensor 110, and measures biological information based on the biological measurement output. The measuring apparatus 100 according to the present embodiment can measure oxygen saturation and a blood flow amount of the subject by using the biological sensor 110. The measuring apparatus 100 according to the present embodiment can measure, for example, percutaneous arterial oxygen saturation ($SpO_2$, S: Saturation, P: Percutaneous or Pulse Oximetry, $O_2$: Oxygen) as a value indicating the oxygen saturation of the subject. However, the biological information measured by the measuring apparatus 100 is not limited to $SpO_2$ and blood flow amount. The measuring apparatus 100 may measure any biological information that can be measured by the biological sensor 110. Hereinafter, $SpO_2$ will also be referred to simply as oxygen saturation. As a value indicating oxygen saturation, there also is $SaO_2$ (S: Saturation, a: artery, $O_2$: Oxygen), that indicates a measured value of oxygen saturation of arterial blood. $SpO_2$ is a method for indirectly measuring $SaO_2$ and, under prepared measurement conditions, both take an approximate value.

The biological sensor 110 acquires the biological measurement output of a measured part of the subject in contact with the measuring apparatus 100. The measured part is any part from which the biological measurement output can be acquired. According to the present embodiment, the measured part is assumed to be a finger in the description below. The measured part may be a wrist, an arm, an ear, a forehead, a neck, a back, a foot, other parts, or any combination thereof, in place of or in addition to a finger. The biological sensor 110 includes an optical emitter and an optical detector. According to the present embodiment, the optical emitter of the biological sensor 110 includes a first laser light source 121 and a second laser light source 122. According to the present embodiment, the optical detector of the biological sensor 110 includes a first optical detector 131 and a second optical detector 132.

Each of the first laser light source 121 and the second laser light source 122 emits laser light of a wavelength capable of detecting a predetermined component in the blood. Each of the first laser light source 121 and the second laser light source 122 is configured as, for example, an LD (Laser Diode). In the present embodiment, a VCSEL (vertical cavity surface emitting laser) diode is used as the laser light source. However, the laser light source may be another laser diode such as a DFB (Distributed Feedback) laser diode or an FP (Fabry-Perot) laser diode.

The first laser light source 121 and the second laser light source 122 emit laser light of different wavelengths. The first laser light source 121 emits laser light of a first wavelength (hereinafter, also referred to as "first laser light"). The first wavelength is a wavelength that exhibits a large difference between absorbance in hemoglobin bonded with oxygen (hereinafter, referred to as "oxyhemoglobin") and absorbance in hemoglobin not bonded with oxygen (hereinafter, referred to as "reduced hemoglobin"). The first wavelength is, for example, 600 nm to 700 nm, and the first laser light is so-called red light. In the present embodiment, the first wavelength will be assumed to be 660 nm in the following description. The second laser light source 122 emits laser light of a second wavelength (hereinafter, also referred to as "second laser light"). The second wavelength is different from the first wavelength. The second wavelength is a wavelength that exhibits a smaller difference between absorbance in oxyhemoglobin and absorbance in reduced hemoglobin than that of the first wavelength. The second wavelength is, for example, 800 nm to 1000 nm, and the second laser light is so-called near infrared light. In the present embodiment, the second wavelength will be assumed to be 850 nm in the following description.

The first optical detector 131 and the second optical detector 132 receive scattered light (detection light) of the measuring light emitted to the measured part and scattered from the measured part as a biological measurement output. Each of the first optical detector 131 and the second optical detector 132 is configured as, for example, a PD (Photo Diode). The biological sensor 110 transmits photoelectric conversion signals of scattered light received by the first optical detector 131 and the second optical detector 132 to the controller 140.

Figure 2:
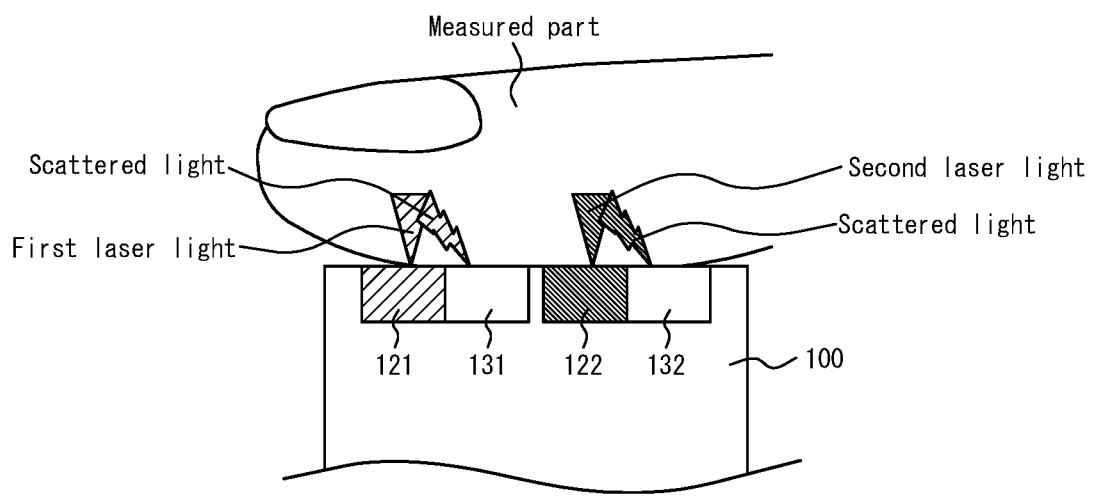
FIG. 2 is a schematic diagram illustrating an example of a usage state of the measuring apparatus of FIG. 1.

FIG. 2 is a schematic diagram illustrating an example of a usage state of the measuring apparatus 100. As schematically illustrated in FIG. 2, the measuring apparatus 100 measures biological information in a state in which a subject causes the measured part to contact a specific location (a measuring unit) on the measuring apparatus 100. The measuring apparatus 100 may measure the biological information in a state in which the subject does not cause the measured part to contact the specific location (the measuring unit) of the measuring apparatus 100.

As schematically illustrated in FIG. 2, the first optical detector 131 receives scattered light of the first laser light emitted by the first laser light source 121 from the measured part. The first optical detector 131 may be configured as a PD capable of detecting light of a wavelength corresponding to scattered first laser light (red light). The second optical detector 132 may be configured as a PD capable of detecting light of a wavelength corresponding to scattered second laser light (near infrared light). In the measuring apparatus 100, the first optical detector 131 and the second optical detector 132 are arranged at positions capable of receiving scattered light of laser light emitted by the first laser light source 121 and the second laser light source 122, respectively.

Here, a relationship between the first laser light, the second laser light, and the light scattered therefrom will be described. For the reduced hemoglobin, the red light of the first laser light is easy to absorb and near infrared light of the second laser light is difficult to absorb. On the other hand, for the oxyhemoglobin, both the red light of the first laser light and the near infrared light of the second laser light are difficult to absorb. That is, the red light of the first laser light is easily absorbed by reduced hemoglobin and hardly absorbed by oxyhemoglobin. The near infrared light of the second laser light is hardly absorbed by reduced hemoglobin and oxyhemoglobin.

Thus, the first laser light is absorbed mainly by reduced hemoglobin and scattered by oxyhemoglobin. Accordingly, the intensity of the scattered first laser light received by the first optical detector 131 as a biological measurement output is an amount originating from the oxyhemoglobin. On the other hand, the second laser light is scattered by both the reduced hemoglobin and the oxyhemoglobin. Accordingly, the intensity of the scattered second laser light received by the second optical detector 132 as a biological measurement output is a total amount originating from the reduced hemoglobin and the oxyhemoglobin.

Referring back to FIG. 1, the controller 140 includes at least one processor 141 configured to control and manage the measuring apparatus 100 in its entirety, including each functional block thereof. The controller 140 includes at least one processor 141 such as a CPU (Central Processing Unit) configured to execute a program defining a control procedure and thus realize its functions. Such a program is stored in, for example, the memory 160 or an external storage medium connected to the measuring apparatus 100.

According to various embodiments, the at least one processor 141 may be configured as a single integrated circuit (IC), or a plurality of communicatively coupled integrated circuits IC and/or a discrete circuit. The at least one processor 141 may be implemented according to various known technologies.

In one embodiment, the processor 141 includes, for example, one or more circuits or units configured to execute one or more data computing procedures or processes by executing instructions stored in an associated memory. In other embodiments, the processor 141 may be firmware (e.g., a discrete logic component) configured to execute one or more data computing procedures or processes.

According to various embodiments, the processor 141 may include one or more processors, controllers, microprocessors, microcontrollers, ASICs (application specific integrated circuits), digital signal processors, programmable logic devices, field programmable gate arrays, any combination of them, or any combination of their configurations, and perform the functions of the controller 140 described below.

The controller 140 calculates values associated with the blood flow amounts based respectively on the output from the first optical detector 131 and the output from the second optical detector 132 (i.e., photoelectric conversion signals of scattered light). The value based on the output from the first optical detector 131 is referred to as a first value, and the value based on the output from the second optical detector 132 is referred to as a second value. The controller 140 can calculate the first value and the second value utilizing Doppler shift.

Here, a measuring method of the first value and the second value utilizing Doppler shift employed by the controller 140 will be described. To measure the first value and the second value, the controller 140 causes the optical emitter (i.e., the first laser light source 121 and the second laser light source 122) to emit laser light to tissue of a living body, and causes the optical detectors (i.e., the first optical detector 131 and the second optical detector 132) to receive scattered light from the tissue of the living body. Then, the controller 140 calculates the first value and the second value based on measurement results of the received laser light.

In the tissue of the living body, scattered light scattered by moving blood cells undergoes a frequency shift (a Doppler shift), due to the Doppler effect, that is proportional to the moving speed of the blood cells in the blood. The controller 140 detects a beat signal generated by light interference between scattered light from static tissue and scattered light from the moving blood cells. The beat signal represents intensity as a function of time. The controller 140 converts the beat signal into a power spectrum which represents power as a function of frequency. In the power spectrum of the beat signal, the Doppler shift frequency is proportional to the moving speed of the blood cells, and the power corresponds to the amount of blood cells. The controller 140 acquires the blood flow amount by multiplying the power spectrum of the beat signal by the frequency and then integrating the multiplication result.

The controller 140 can calculate the first value P1 [ml/min] from, for example, $P1=K \cdot \int f \cdot P(f) \, df/\langle I \times I \rangle$, where K represents a proportionality constant, $I \times I$ represents a mean square of the intensity of the received light signal, f represents the frequency, and P(f) represents a power spectrum of the beat signal. The controller 140 may calculate the first value P1 from, for example, $P1=\int f \cdot P(f) \, df/\langle I \times I \rangle$ or $P1=\int f \cdot P(f) \, df$. That is, the controller 140 may calculate the first value P1 by using any one of $P1=K \cdot \int f \cdot P(f) \, df/\langle I \times I \rangle$, $P1=\int f \cdot P(f) \, df/\langle I \times I \rangle$, and $P1=\int f \cdot P(f) \, df$. The same applies to the second value P2. That is, the controller 140 may calculate the second value P2 from any one of $P2=K \cdot \int f \cdot P(f) \, df/\langle I \times I \rangle$, $P2=\int f \cdot P(f) \, df/\langle I \times I \rangle$, and $P2=\int f \cdot P(f) \, df$.

As described above, because the output from the first optical detector 131 originates from the amount of oxyhemoglobin in the blood, the first value indicates a value based on a flow rate of the oxyhemoglobin. Because the output from the second optical detector 132 originates from the total amount of hemoglobin in the blood, the second value indicates a value based on a flow rate of all hemoglobin in the blood. Because the value calculated based on the flow rate of all hemoglobin in the blood corresponds to the blood flow amount of the subject, the second value indicates the blood flow amount of the subject. Accordingly, the controller 140 can calculate the blood flow amount of the subject by calculating the second value. Thus, the measuring apparatus 100 can measure the blood flow amount of the subject.

The controller 140 calculates $SpO_2$ of the subject based on the first value and the second value. The controller 140 can calculate $SpO_2$ based on a ratio of the first value to the second value.

Here, the calculation method for $SpO_2$ employed by the controller 140 will be described in detail. $SpO_2$ is calculated from the following formula: $\{HbO_2/(Hb+HbO_2)\} \times 100$, where $HbO_2$ represents the amount of oxygenated hemoglobin, and Hb represents the amount of reduced hemoglobin (for example, see PTL 1). In this formula, $HbO_2$ represents the amount of oxygenated hemoglobin, and $(Hb+HbO_2)$ represents a total amount of oxygenated hemoglobin and reduced hemoglobin. Thus, in the present embodiment, $HbO_2$ can correspond to the first value calculated based on the flow rate of oxyhemoglobin, and $(Hb+HbO_2)$ can correspond to the second value calculated based on the flow rate of all hemoglobin in the blood. Accordingly, when the first value is substituted for $HbO_2$ and the second value is substituted for $(Hb+HbO_2)$ in the above formula, the index indicated by $SpO_2$ can be calculated from, for example, (first value/second value)×100. In the present embodiment, the controller 140 calculates the index indicating $SpO_2$ from the formula: (first value/second value)×100. Because the controller 140 calculates the index indicating $SpO_2$ as described above, the measuring apparatus 100 can measure the $SpO_2$ of the subject. Here, the formula (first value/second value)× 100 is used to calculate the index indicating $SpO_2$. Thus, the formula (first value/second value)×100, or a value acquired by performing predetermined weighting of the value of (first value/second value), e.g., by multiplying a coefficient, or a value acquired by using a table for converting the value (first value/second value) into $SpO_2$ can be used as $SpO_2$.

Further, the controller 140 may estimate the likelihood that the subject gets altitude sickness (also called altitude impairment) based on the blood flow amount and the $SpO_2$ of the subject. Altitude sickness is more likely when $SpO_2$ decreases or when dehydrated. When the subject is dehydrated, insufficient moisture in the blood causes poor blood flow (decrease of the blood flow amount). Thus, the controller 140 can estimate the likelihood that the subject gets altitude sickness based on changes in the blood flow amount and $SpO_2$. The controller 140 may estimate the likelihood of altitude sickness by, for example, weighting the blood flow amount and $SpO_2$ using a predetermined algorithm. The measuring apparatus 100 according to the present embodiment can measure both $SpO_2$ and blood flow amount and thus is capable of estimating the likelihood of altitude sickness based on the two indexes, $SpO_2$ and the blood flow amount. Thus, the measuring apparatus 100 according to the present embodiment can more accurately estimate a likelihood of altitude sickness than an apparatus that estimates the likelihood of altitude sickness based on $SpO_2$ alone.

The notification interface 150 notifies of information using a sound, a vibration, an image, or the like. The notification interface 150 may include a speaker, a vibrator, and a display device. The display device may be, for example, an LCD (Liquid Crystal Display), an OELD (Organic Electro-Luminescence Display), an IELD (Inorganic Electro-Luminescence Display), or the like. The notification interface 150 may notify, for example, a measurement result of $SpO_2$ and/or a blood flow amount. The notification interface 150 may notify, for example, information regarding a likelihood of altitude sickness.

The memory 160 may be configured as a semiconductor memory, a magnetic memory, or the like. The memory 160 stores various information and a program for operating the measuring apparatus 100. The memory 160 may also function as a working memory. The memory 160 may store, for example, $SpO_2$ and the blood flow amount of the subject calculated by the controller 140 as history information.

Figure 3:
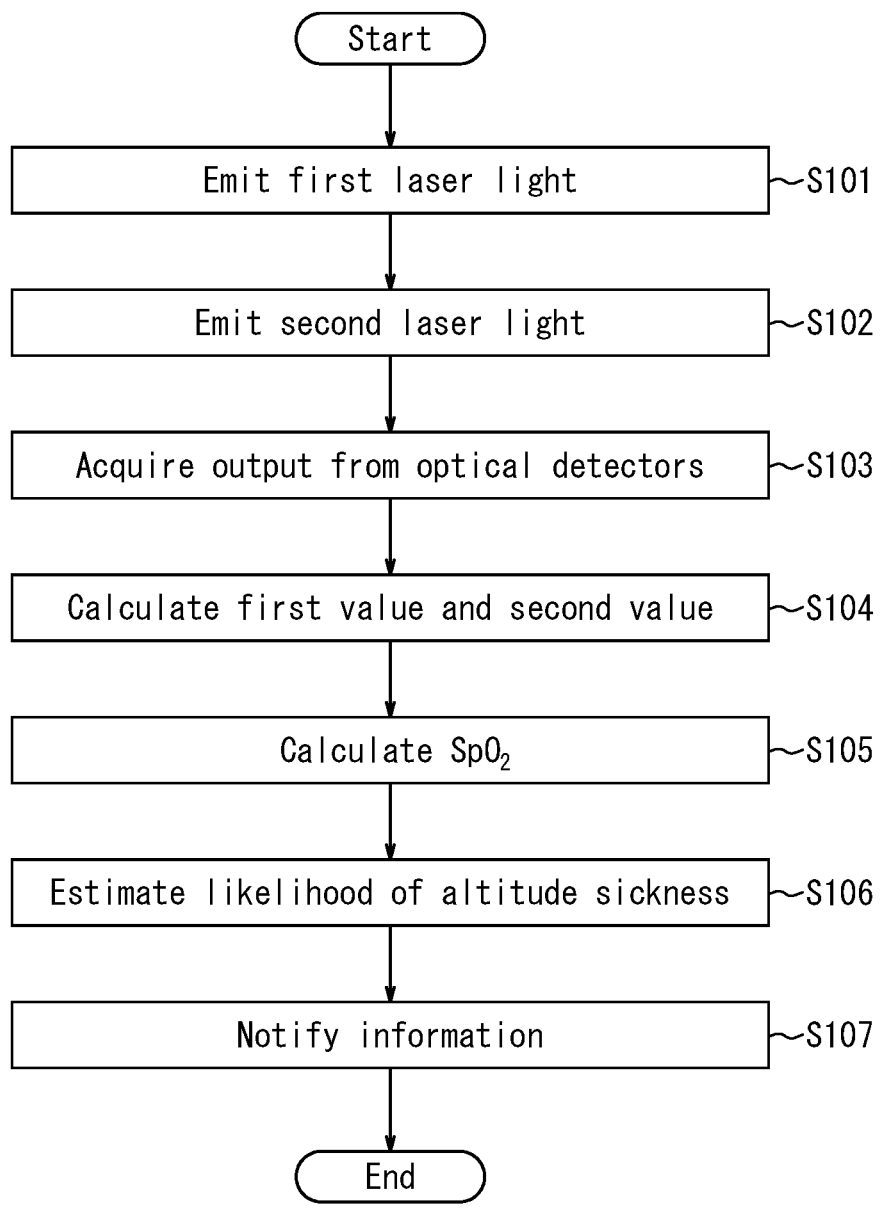
FIG. 3 is a flowchart illustrating an example of operations performed by a controller of FIG. 1.

Next, an example of operations performed by the controller 140 of the measuring apparatus 100 will be described with reference to the flowchart illustrated in FIG. 3. The controller 140 may repeat the flow illustrated in FIG. 3 when the measuring apparatus 100 is activated or when there is a predetermined input operation for starting the measuring operation. In a case in which the controller 140 has functionality which is able to detect whether the measured part is in contact with the measuring unit, the controller 140 may execute the flow illustrated in FIG. 3 when it is determined that the measured part is in contact with the measurement unit.

The controller 140 causes the first laser light source 121 to emit the first laser light (step S101).

The controller 140 causes the second laser light source 122 to emit the second laser light (step S102).

When the first laser light is emitted in step S101, the first optical detector 131 receives scattered light from the measured part. When the second laser light is emitted in step S102, the second optical detector 132 receives scattered light from the measured part. The first optical detector 131 and the second optical detector 132 transmit photoelectric conversion signals of the respective scattered light to the controller 140.

The controller 140 acquires the outputs from the first optical detector 131 and the second optical detector 132 (step S103).

The controller 140 calculates the first value based on the output acquired from the first optical detector 131 and the second value based on the output acquired from the second optical detector 132 (step S104).

The controller 140 calculates indexes indicating $SpO_2$ based on the first value and the second value calculated in step S104, and calculates $SpO_2$ from the indexes corresponding to $SpO_2$ (step S105).

The controller 140 estimates the likelihood that the subject gets altitude sickness based on the blood flow amount (i.e., the second value) and $SpO_2$ (step S106).

The controller 140 causes the notification interface 150 to notify the blood flow amount and $SpO_2$, as well as the information regarding the likelihood of altitude sickness (step S107).

As described above, the measuring apparatus 100 according to the present embodiment emits laser light to the measured part and calculates the first value and the second value based on the intensities of scattered laser light from the measured part. The measuring apparatus 100 calculates $SpO_2$ based on the first value and the second value. As described above, the measuring apparatus 100 uses laser light to acquire the biological measurement output. Because laser light has high directionality and wavelength and phase are aligned, the measuring apparatus 100 can more accurately measure $SpO_2$ than a case in which, for example, light of a wide wavelength band is used instead of laser light. Thus, according to the measuring apparatus 100, usability is improved.

The measuring apparatus 100 can measure both the blood flow amount and $SpO_2$ and thus eliminates the necessity to measure the blood flow amount and $SpO_2$ by using individual apparatuses. Thus, the measuring apparatus 100 improves the convenience and usability for the subject.

Second Embodiment

Figure 4:
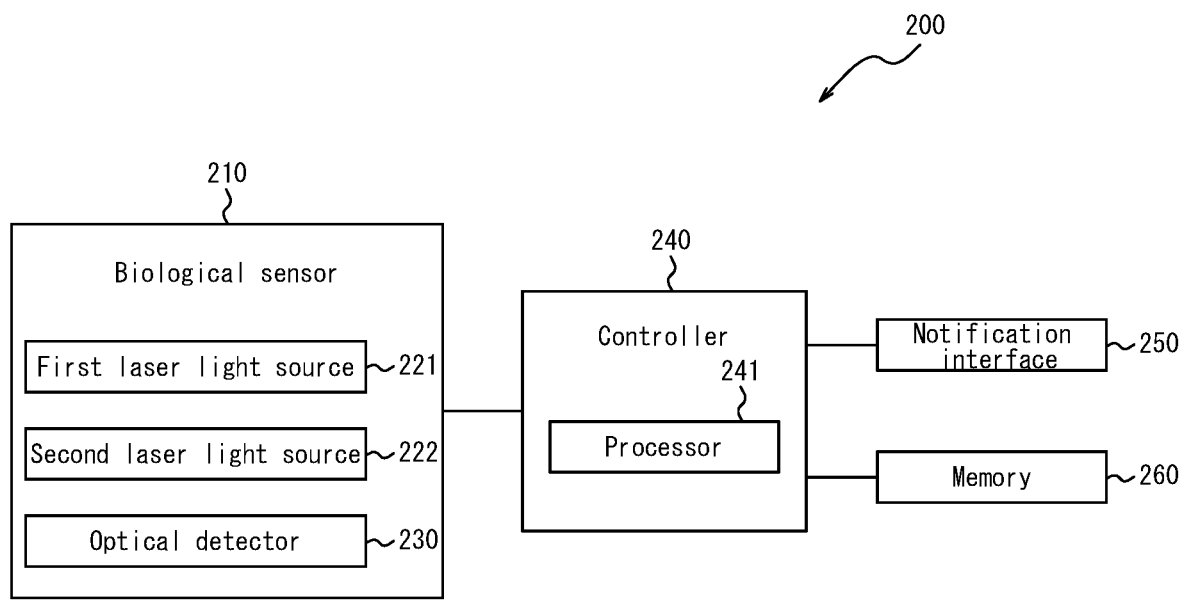
FIG. 4 is a functional block diagram illustrating a schematic configuration of a measuring apparatus according to a second embodiment.

FIG. 4 is a functional block diagram illustrating a schematic configuration of a measuring apparatus 200 according to a second embodiment. The measuring apparatus 200 according to the present embodiment includes a biological sensor 210, a controller 240, a notification interface 250, and a memory 260.

The measuring apparatus 200 according to the second embodiment differs from the measuring apparatus 100 according to the first embodiment in that the biological sensor 210 includes only one optical detector 230, whereas the biological sensor 110 includes two optical detectors, i.e., the first optical detector 131 and the second optical detector 132.

According to the present embodiment, that is, the biological sensor 210 includes two light sources, i.e., a first laser light source 221 and a second laser light source 222, and an optical detector 230. The functions of the first laser light source 221 and the second laser light source 222 are similar to those of the first laser light source 121 and the second laser light source 122, respectively, of the first embodiment. That is, the first laser light source 221 emits first laser light, and the second laser light source 222 emits second laser light. The first laser light source 221 emits the first laser light and the second laser light source 222 emits the second laser light at different timings. For example, the first laser light source 221 and the second laser light source 222 alternately emit laser light. That is, in a measuring operation by the measuring apparatus 200, the first laser light and the second laser light are alternately emitted to the measured part at, for example, predetermined intervals.

The optical detector 230 is configured as, for example, a so-called multi-frequency-responsive PD capable of detecting scattered light of the wavelengths corresponding to both the first laser light (red light) and the second laser light (near infrared light). Thus, the second optical detector 232 detects scattered first laser light when the first laser light is emitted to the measured part, and detects scattered second laser light when the second laser light is emitted to the measured part. The biological sensor 210 transmits a photoelectric conversion signal of scattered light received by the optical detector 230 to the controller 240.

Figure 5:
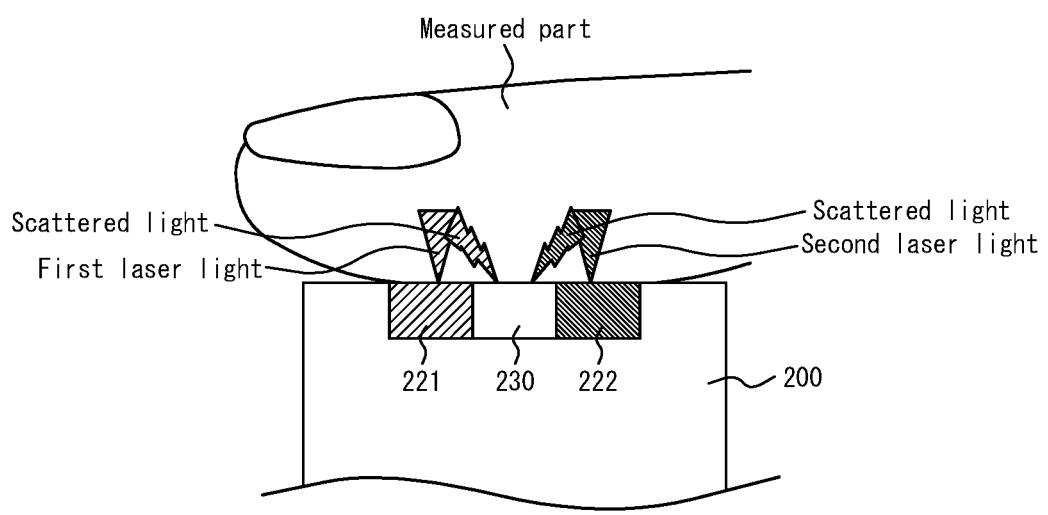
FIG. 5 is a schematic diagram illustrating an example of a usage state of the measuring apparatus of FIG. 4.

FIG. 5 is a schematic diagram illustrating an example of a usage state of the measuring apparatus 200. As schematically illustrated in FIG. 5, the optical detector 230 receives scattered light of the first laser light emitted by the first laser light source 221 and scattered light of the second laser light emitted by the second laser light source 222 from the measured part. Because the first laser light and the second laser light are alternately emitted as described above, the optical detector 230 alternately receives scattered first laser light and scattered second laser light. Although FIG. 5 illustrates the first laser light, the second laser light, scattered first laser light, and scattered second laser light, in reality either the first laser light or the second laser light is emitted to the measured part at a certain point in time, and the optical detector 230 receives scattered light of laser light being emitted. The optical detector 230 is arranged at a position of the measuring apparatus 200 capable of receiving scattered light of laser light emitted by the first laser light source 221 and scattered light of laser light emitted by the second laser light source 222.

Referring back to FIG. 4, the controller 240 includes at least one processor 241 configured to control and manage the measuring apparatus 200 in its entirety, including each functional block thereof. Functions of the controller 240 and the processor 241 are similar to those of the controller 140 and the processor 141, respectively, of the first embodiment. Thus, detailed descriptions will be omitted here. Also, functions of the notification interface 250 and the memory 260 are similar to those of the notification interface 150 and the memory 160, respectively, of the first embodiment. Thus, detailed descriptions will be omitted here.

In the measuring apparatus 200 according to the present embodiment, the controller 240 measures the blood flow amount and $SpO_2$ by performing operations similar to the operations described with reference to FIG. 3, and estimates the likelihood that the subject gets altitude sickness. In the present embodiment, the controller 240 acquires the output from the optical detector 230 in step S103. The controller 240 calculates the first value or the second value, depending on whether the output acquired from the optical detector 230 corresponds to scattered first laser light or scattered second laser light in step S104.

As described above, the measuring apparatus 200 according to the present embodiment emits laser light to the measured part and measures $SpO_2$. Thus, the measuring apparatus 200 can more accurately measure $SpO_2$ than an apparatus that uses, for example, light of a wide wavelength band. In this way, according to the measuring apparatus 200, usability is improved. The measuring apparatus 100 according to the present embodiment can receive scattered first laser light and scattered second laser light by using the optical detector 230 that corresponds to multiple frequencies. Thus, the biological sensor 210 and the measuring apparatus 200 may be downsized more than those of an apparatus that includes two individual optical detectors to receive scattered first laser light and scattered second laser light, respectively.

Third Embodiment

Figure 6:
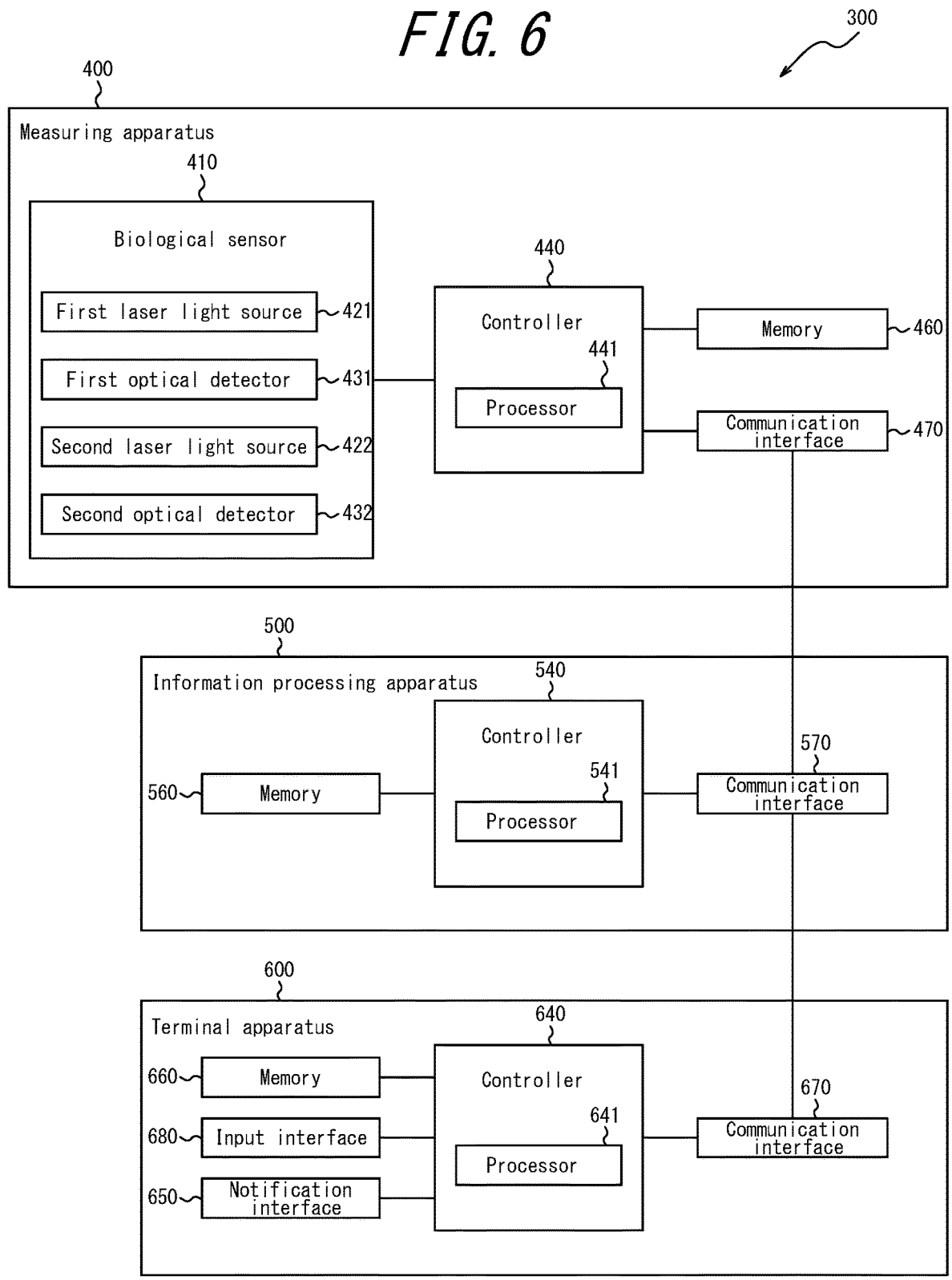
FIG. 6 is a functional block diagram illustrating a schematic configuration of a measuring system according to a third embodiment.

FIG. 6 is a functional block diagram illustrating a schematic configuration of a measuring system 300 according to a third embodiment. The measuring system 300 includes a measuring apparatus 400, an information processing apparatus 500, and a terminal apparatus 600. The information processing apparatus 500 is communicably connected to the measuring apparatus 400 and the terminal apparatus 600 via wired communication, wireless communication, or a combination thereof. The measuring apparatus 400 and the terminal apparatus 600 may directly communicate with each other. The network connecting the measuring apparatus 400, the information processing apparatus 500, and the terminal apparatus 600 together may be the Internet, a wireless LAN, or the like.

The measuring apparatus 400 is an apparatus configured to measure a biological measurement output by emitting measuring light to the measured part. The measuring apparatus 400 may transmit information regarding the biological measurement output to the information processing apparatus 500.

The information processing apparatus 500 may be configured as, for example, a server apparatus such as a computer. The information processing apparatus 500 may calculate the blood flow amount and $SpO_2$ of the subject based on the information regarding the biological measurement output acquired from the measuring apparatus 400. The information processing apparatus 500 may estimate the likelihood that the subject gets altitude sickness. The information processing apparatus 500 may store the calculation results of the blood flow amount and $SpO_2$, and information regarding the likelihood of altitude sickness. The information processing apparatus 500 may transmit the calculation results of the blood flow amount and $SpO_2$, and the information regarding the likelihood of altitude sickness, to the terminal apparatus 600.

The terminal apparatus 600 may be configured as, for example, a personal computer, a smartphone, a tablet computer, or the like. The terminal apparatus 600 may be owned by the subject. The terminal apparatus 600 may perform notification, based on the calculation results of the blood flow amount and $SpO_2$ and the information regarding the likelihood of altitude sickness acquired from the information processing apparatus 500.

The measuring apparatus 400 includes a biological sensor 410, a controller 440, a and a memory 460. The biological sensor 410 includes a first laser light source 421, a second laser light source 422, a first optical detector 431, and a second optical detector 432. Functions of the first laser light source 421, the second laser light source 422, the first optical detector 431, and the second optical detector 432 are similar to the functions of the first laser light source 121, the second laser light source 122, the first optical detector 131, and the second optical detector 132, respectively, of the first embodiment. The measuring apparatus 400 according to the present embodiment can acquire a biological measurement output in a manner similar to the measuring apparatus 100 of the first embodiment.

The controller 440 includes at least one processor 441 configured to control and manage the measuring apparatus 400 in its entirety, including each functional block thereof. The controller 440 includes at least one processor 441 such as a CPU configured to execute a program defining a control procedure and thus realize its function. Such a program is stored in, for example, the memory 460 or an external storage medium connected to the measuring apparatus 400. The processor 441 may have a configuration similar to, for example, the configuration of the processor 141 of the first embodiment. Thus, detailed descriptions will be omitted here. The controller 440 causes the biological sensor 410 to acquire the biological measurement output and transmits information regarding the biological measurement output to the information processing apparatus 500 via the communication interface 470.

The memory 460 may be configured as a semiconductor memory, a magnetic memory, or the like. The memory 460 stores various information and/or a program for operating the measuring apparatus 400. The memory 460 may also function as a working memory. The memory 460 may store, for example, data for the information regarding the biological measurement output (i.e., intensities of scattered light) acquired by the biological sensor 410.

The communication interface 470 transmits and receives various information by performing wired communication, wireless communication, or a combination thereof, with the information processing apparatus 500. For example, the communication interface 570 transmits information regarding the biological measurement output measured by the measuring apparatus 400 to the information processing apparatus 500.

The information processing apparatus 500 includes a controller 540, a memory 560, and a communication interface 570.

The controller 540 includes at least one processor 541 configured to control and manage the information processing apparatus 500 in its entirety, including each functional block thereof. The controller 540 includes at least one processor 541 such as a CPU configured to execute a program defining a control procedure and thus realize its functions. Such a program is stored in, for example, the memory 560 or an external storage medium connected to the information processing apparatus 500. The processor 541 may have a configuration similar to, for example, the configuration of the processor 141 of the first embodiment. Thus, detailed descriptions will be omitted here. The controller 540 may calculate the blood flow amount and $SpO_2$ of the subject based on the information regarding the biological measurement output acquired from the measuring apparatus 400. The controller 540 may estimate the likelihood that the subject gets altitude sickness. The calculation method of the blood flow amount and $SpO_2$ and the estimation method of the likelihood of altitude sickness are similar to those described in the first embodiment. Thus, detailed descriptions will be omitted.

The memory 560 may be configured as a semiconductor memory, a magnetic memory, or the like. The memory 560 stores various information and/or programs for operating the information processing apparatus 500. The memory 560 may also function as a working memory. The memory 560 may store, for example, information regarding the biological measurement output acquired from the measuring apparatus 400. The memory 160 may store, for example, the blood flow amount and $SpO_2$ calculated by the controller 540 as well as various information used for the estimation of the likelihood of altitude sickness.

The communication interface 570 transmits and receives various information by performing wired communication, wireless communication, or a combination thereof with the measuring apparatus 400 and the terminal apparatus 600. For example, the communication interface 570 receives information regarding the biological measurement output from the measuring apparatus 400. For example, the communication interface 570 transmits the blood flow amount and $SpO_2$ calculated by the information processing apparatus 500 and the information regarding the likelihood of altitude sickness to the terminal apparatus 600.

The terminal apparatus 600 includes a controller 640, a notification interface 650, a memory 660, a communication interface 670, and an input interface 680.

The controller 640 includes at least one processor 641 configured to control and manage the terminal apparatus 600 in its entirety, including each functional block thereof. The controller 640 includes at least one processor 641 such as a CPU configured to execute a program defining a control procedure and thus realize its functions. Such a program is stored in, for example, a memory 660 or an external storage medium connected to the terminal apparatus 600. The processor 641 may have a configuration similar to, for example, the configuration of the processor 141 of the first embodiment. Thus, detailed descriptions will be omitted here. The controller 640 may cause the notification interface 650 to notify of the blood flow amount and $SpO_2$ acquired from the information processing apparatus 500 together with the information regarding the likelihood altitude sickness.

The notification interface 650 notifies the information using a sound, a vibration, an image, or the like. The functions and the configuration of the notification interface 650 are similar to those of the notification interface 150 described in the first embodiment. Thus, detailed descriptions will be omitted here.

The memory 660 may be configured as a semiconductor memory, a magnetic memory, or the like. The memory 660 stores various information and/or programs for operating the terminal apparatus 600. The memory 660 may also function as a working memory. The memory 660 may store, for example, the blood flow amount and $SpO_2$ acquired from the information processing apparatus 500 as well as the information regarding the likelihood of altitude sickness.

The communication interface 670 transmits and receives various information by performing wired communication, wireless communication, or a combination thereof with the information processing apparatus 500. For example, the communication interface 670 receives the blood flow amount and $SpO_2$ acquired from the information processing apparatus 500 and the information regarding the likelihood of altitude sickness from the information processing apparatus 500.

The input interface 680 is configured to receive an input operation from a user (e.g., the subject) of the terminal apparatus 600 and configured as, for example, an operation button (an operation key). The input interface 680 may be configured as a touch panel configured to display an operation key for receiving an input operation from the user in a portion of the display device and may receive a touch input operation made by the user.

Figure 7:
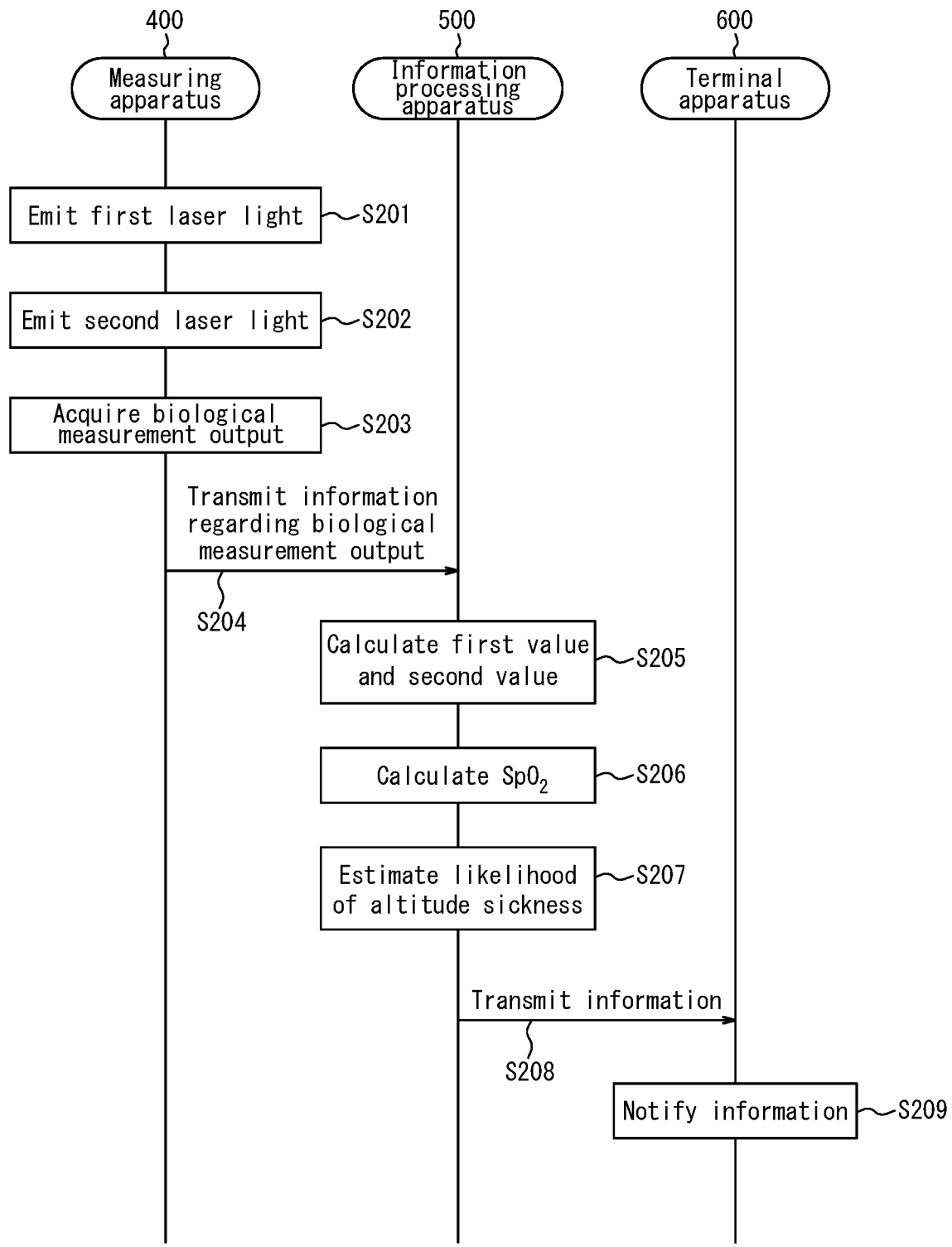
FIG. 7 is a sequence diagram illustrating an example of a control procedure of the measuring system 300 of FIG. 6.

FIG. 7 is a sequence diagram illustrating an example of a control procedure performed by the measuring system 300. The procedure illustrated in FIG. 7 is executed when, for example, the measuring apparatus 400 is activated or a predetermined input operation for starting the measuring operation is performed. In a case in which the controller 440 of the measuring apparatus 400 has functionality which is able to detect whether the measured part is in contact with the measuring unit, the procedure illustrated in FIG. 7 may be executed when it is determined that the measured part is in contact with the measuring unit.

The measuring apparatus 400 causes the first laser light source 421 to emit the first laser light (step S201).

The measuring apparatus 400 causes the second laser light source 422 to emit the second laser light (step S202).

The measuring apparatus 400 acquires the biological measurement output from the first optical detector 431 and the second optical detector 432 (step S203).

The measuring apparatus 400 transmits the information regarding the biological measurement output to the information processing apparatus 500 via the communication interface 470 (step S204).

Upon receiving the information regarding the biological measurement output from the measuring apparatus 400, the information processing apparatus 500 calculates the first value and the second value based on the biological measurement outputs (step S205).

The information processing apparatus 500 calculates $SpO_2$ based on the first value and the second value calculated in step S205 (step S206).

The information processing apparatus 500 estimates the likelihood that the subject gets altitude sickness based on the blood flow amount (i.e., the second value) and $SpO_2$ (step S207).

The information processing apparatus 500 transmits the blood flow amount, $SpO_2$, and the information regarding the likelihood of altitude sickness to the terminal apparatus 600 via the communication interface 570 (step S208).

Upon receiving the blood flow amount, $SpO_2$, and the information regarding the likelihood of altitude sickness from the information processing apparatus 500, the terminal apparatus 600 causes the notification interface 650 to notify of the blood flow amount, $SpO_2$, and the information regarding the likelihood of altitude sickness (step S209).

According to the present embodiment, the biological sensor 410 of the measuring apparatus 400 has been described as having a configuration similar to that of the biological sensor 110 of the first embodiment. However, the biological sensor 410 may have a configuration similar to that of the biological sensor 210 of the second embodiment.

In the present embodiment, the information processing apparatus 500 has been described as calculating the blood flow amount and SpO$_2$ and estimating the likelihood of altitude sickness. However, for example, the measuring apparatus 200 may perform the calculation of the blood flow amount and SpO$_2$ and the estimation of the likelihood of altitude sickness. In this case, the measuring apparatus 400 may transmit the calculation results of the blood flow amount and SpO$_2$ and the estimation result of the likelihood of altitude sickness to the information processing apparatus 500. The measuring system 300 does not need to include the information processing apparatus 500. In this case, the measuring apparatus 400 may transmit the calculation results of the blood flow amount and SpO$_2$ and the estimation result of the likelihood of altitude sickness to the terminal apparatus 600.

As described above, the measuring system 300 according to the present embodiment calculates SpO$_2$ based on laser light emitted to the measured part and thus can more accurately measure SpO$_2$ than an apparatus using, for example, light of a wide wavelength band. Thus, according to the measuring system 300 usability is improved.

Several embodiments have been described in order to provide a complete and clear disclosure the present disclosure. However, the appended claims are not limited to the above embodiments and should be constructed so as to encompass all modifications and alternative configurations that can be created by those skilled in the art within the scope of the fundamentals shown in this description. Each of the elements of the embodiments may be combined in any appropriate manner.

The measuring apparatuses (the measuring apparatuses 100, 200, and 400) described in the above embodiments can be mounted in various devices.

Figure 8:
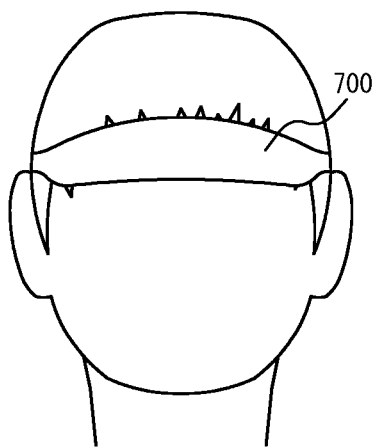
FIG. 8 is a schematic diagram illustrating an example of a cerebral blood flow meter.

For example, the measuring apparatus 100, 200, or 400 may be mounted in a cerebral blood flow meter for measuring cerebral blood flow. A cerebral blood flow meter is a device for measuring cerebral blood flow by emitting laser light to the brain. As illustrated in FIG. 8, for example, a subject uses a cerebral blood flow meter 700 by wrapping a measuring member having a strip-like shape about the head. The measuring apparatus 100, 200, or 400 may be mounted in the measuring member. When the measuring apparatus 100, 200, or 400 is mounted in the cerebral blood flow meter 700, the subject can activate the cerebral blood flow meter 700 and the measuring apparatus 100, 200, or 400 in a state in which the measuring member of the cerebral blood flow meter 700 is wrapped about the head. Thus, the subject can measure a cerebral blood flow, a blood flow amount, and SpO$_2$ simultaneously. In this case, the cerebral blood flow meter 700 can estimate the likelihood that the subject gets altitude sickness based on the cerebral blood flow, the blood flow amount, and SpO$_2$. Thus, the estimation accuracy is better than that of a case in which SpO$_2$ alone is used to estimate the likelihood of altitude sickness.

Figure 9:
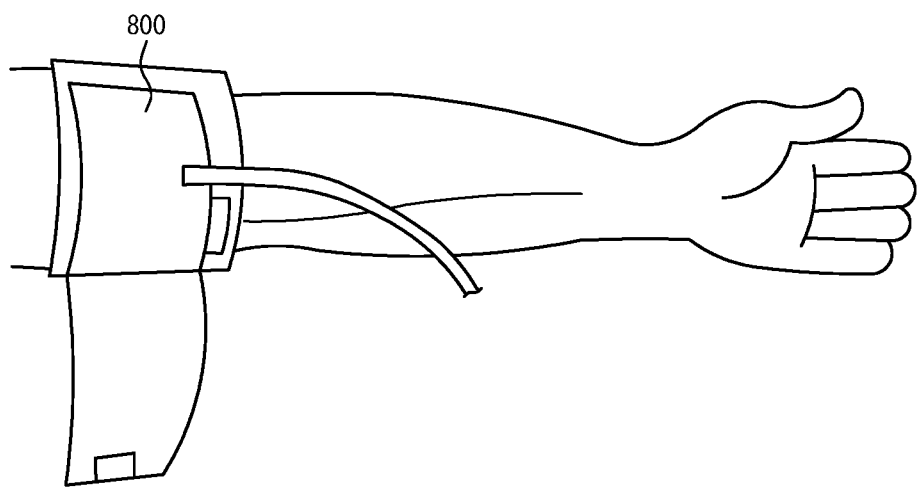
FIG. 9 is a schematic diagram illustrating an example of a sphygmomanometer.

For example, the measuring apparatus 100, 200, or 400 may be mounted in a sphygmomanometer for measuring blood pressure. A sphygmomanometer may be, for example, a known upper-arm type sphygmomanometer for measuring blood pressure in an upper arm by using a cuff (an arm band). As illustrated in FIG. 9, for example, a subject uses a sphygmomanometer 800 by wrapping a cuff about the upper arm. The measuring apparatus 100, 200, or 400 may be mounted in the cuff. When the measuring apparatus 100, 200, or 400 is mounted in the sphygmomanometer 800, the subject can activate the sphygmomanometer 800 and the measuring apparatus 100, 200, or 400 in a state in which the cuff is wrapped about the upper arm. Thus, the subject can measure blood pressure, a blood flow amount, and SpO$_2$ simultaneously. In this case, the sphygmomanometer 800 can estimate the likelihood that the subject gets altitude sickness based on the blood pressure, the blood flow amount, and SpO$_2$. Thus, the estimation accuracy is better than that of a case in which SpO$_2$ alone is used to estimate the likelihood of altitude sickness.

Figure 10:
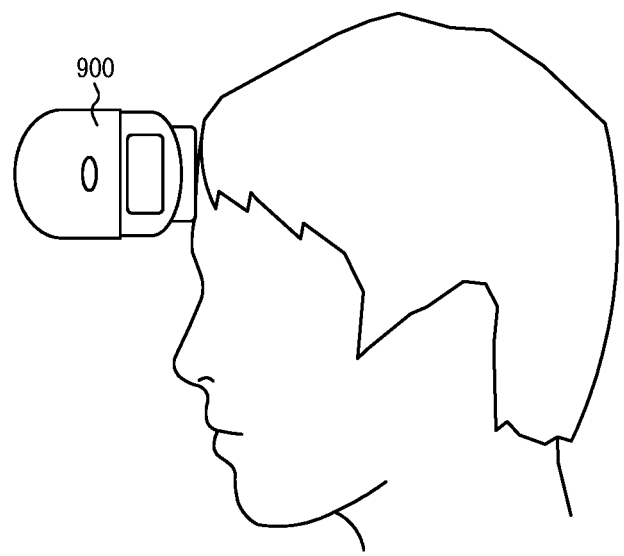
FIG. 10 is a schematic diagram illustrating an example of a thermometer.

For example, the measuring apparatus 100, 200, or 400 may be mounted in a thermometer for measuring body temperature. As illustrated in FIG. 10, for example, a thermometer 900 is brought into contact with human skin to measure skin temperature. When the measuring apparatus 100, 200, or 400 is mounted in the thermometer 900, the subject can activate the measuring apparatus 100, 200, or 400 when bringing the thermometer 900 into contact with the skin to measure body temperature. Thus, the subject can measure body temperature, a blood flow amount, and SpO$_2$ simultaneously. In this case, the thermometer 900 can estimate the likelihood that the subject gets altitude sickness based on the body temperature, the blood flow amount, and SpO$_2$. Thus, the estimation accuracy is better than that of a case in which SpO$_2$ alone is used to estimate the likelihood of altitude sickness.

The measuring apparatus 100, 200, or 400 may be mounted in an apparatus capable of measuring information regarding a living body, other than the cerebral blood flow meter 700, the sphygmomanometer 800, and the thermometer 900.

The controller of each of the embodiments has been described as estimating the likelihood that the subject gets altitude sickness based on the blood flow amount and SpO$_2$. However, the controller of each of the embodiments may detect a blood pressure, a dehydration state, a relaxed state, an autonomic state, or other symptoms such as a heart disease, based on at least one of the blood flow amount and SpO$_2$.

Although in the above embodiment the measured part is described as a finger, the measured part does not need to be a finger. The measured part may be, for example, a wrist, an arm, an ear, the forehead, the neck, the back, a foot, other parts, or any combination thereof, as described above.

Figure 11:
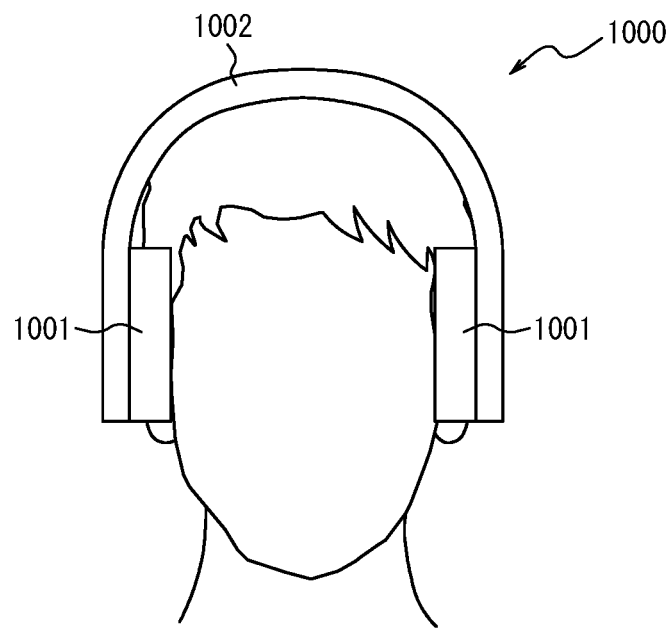
FIG. 11 is a schematic diagram illustrating an example of a wearing state of a measuring instrument equipped with a measuring apparatus for measuring at a temple as a measured part.

Here, a configuration of a measuring apparatus in which the measured part is a temple will be described in detail. FIG. 11 is a schematic diagram of an example wearing state of a measuring instrument 1000 that includes a measuring apparatus for measuring the temple as the measured part. The measuring instrument 1000 includes two holding portions 1001 and a head band 1002 for coupling the two holding portions 1001 together.

In a wearing state of the measuring instrument 1000, the two holding portions 1001 come into contact with the left and right temples of the subject and maintain the wearing state. The holding portions 1001 may be shaped to avoid covering the subject's ears. For example, the holding portions 1001 may be configured to contact the temples above the ear. In this case, the subject's ears are not covered in the wearing state of the measuring instrument 1000, allowing the subject to hear ambient sounds. Accordingly, the safety of the subject can be easily ensured as compared to a case in which the subject's ears are covered.

The head band 1002 may have, for example, an arcuate shape as illustrated in FIG. 11. The measuring instrument 1000 is worn by the subject in such a manner that, for example, the head band 1002 is positioned on top of the head. The head band 1002 may be designed such that, for example, the length thereof is adjustable to the subject's head. The head band 1002 may be made from a member having rigidity such as stainless steel or carbon fiber. The head band 1002 may maintain the wearing state of the measuring instrument 1000 by pressing the holding portions 1001 against the subject's body.

At least one of the holding portions 1001 includes a measuring apparatus. The measuring apparatus included in the holding portion 1001 may be, for example, any one of the measuring apparatuses of the first to third embodiments described above. In the following description, the holding portion 1001 will be described as including the measuring apparatus 200 described in the second embodiment.

Figure 12:
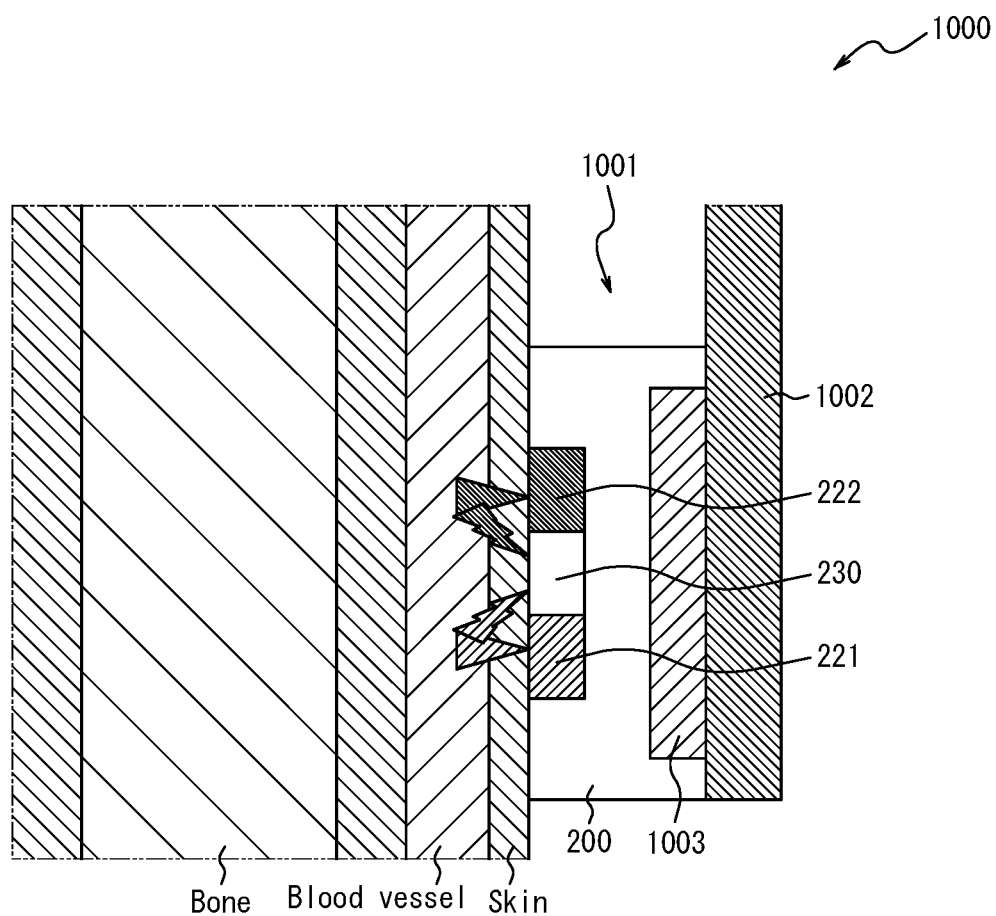
FIG. 12 is a diagram illustrating a cross-section of a portion of the measuring equipment illustrated in FIG. 11.

FIG. 12 is a partial cross-sectional view of the measuring instrument 1000 illustrated in FIG. 11 and schematically illustrates the holding portions 1001 having the measuring apparatus 200. As illustrated in FIG. 12, each of the holding portions 1001 is provided with the measuring apparatus 200 which includes the first laser light source 221, the second laser light source 222, and the optical detector 230 as described in the second embodiment. In a wearing state of the measuring instrument 1000, laser light (measuring light) emitted by the first laser light source 221 and the second laser light source 222 irradiates the superficial temporal artery. The optical detector 230 receives scattered measuring light from the superficial temporal artery. That is, the measuring instrument 1000 calculates the blood flow amount and $SpO_2$ by using scattered light from the superficial temporal artery. The blood vessels of the superficial temporal artery are larger than, for example, blood vessels in a fingertip and thus facilitate acquisition of the biological information. Because the blood vessels of the superficial temporal artery are larger than, for example, blood vessels in a fingertip, the blood flow tends to be stable. Thus, the blood flow amount and $SpO_2$ can be more accurately measured by emitting the measuring light to the superficial temporal artery and obtaining biological information.

As illustrated in FIG. 12, the measuring apparatus 200 may be connected to the head band 1002 via a connecting portion 1003. The connecting portion 1003 functions as a buffer for reducing vibration transmitted from the head band 1002 to the measuring apparatus 200. The connecting portion 1003 functions as, for example, a damper. The connecting portion 1003 may be made of a resilient material capable of reducing vibration. The connecting portion 1003 may be made of spring, rubber, silicone resin, gel, fabric, sponge, paper, other members, or any combination thereof. The connecting portion 1003 may be, for example, a fluid-filled damper containing a fluid (i.e. liquid or gas). The fluid may be a viscous liquid. The connecting portion 1003 reduces vibration of the head band 1002 transmitted to the measuring apparatus 200. Thus, the measuring apparatus 200 hardly changes its position with respect to the measured part. Accordingly, the measuring apparatus 200 can more accurately measure a blood flow amount and $SpO_2$.

In the measuring instrument 1000, the measuring apparatus included in the holding portions 1001 is not limited to the measuring apparatus 200 described in the second embodiment and may be, for example, the measuring apparatus 100 described in the first embodiment. One of the holding portions 1001 may include the first laser light source 121 and the first optical detector 131 described in the first embodiment, and the other one of the holding portions 1001 may include the second laser light source 122 and the second optical detector 132 described in the first embodiment.

In the above embodiments, it has been described that the first laser light source and the second laser light source of the biological sensor emit laser light. However, one of the first laser light source and the second laser light source may be configured as a light source other than the laser light source, such as an LED (Light Emitting Diode). When an LED light source is used in place of the first laser light source, the LED light source emits red light. When the LED light source is used in place of the second laser light source, the LED light source emits near infrared light. When the LED light source is used in place of the laser light source, the controller calculates the first value P1 and the second value P2 based on, for example, an intensity of light received by the optical detector corresponding to an amount of light emitted by the LED light source. For example, when an LED light source is used in place of the first laser light source, the controller calculates the first value P1 based on the intensity of the light received by the first optical detector corresponding to the amount of the light emitted by the LED light source. A relationship between a ratio of the intensity of the light corresponding to the amount of emitted light and the first value P1 may be stored as, for example, a table in a memory. The controller can calculate the first value P1 by referring to the table.

The invention claimed is:

1. A measuring apparatus comprising:
    a first laser light source for emitting laser light of a first wavelength;
    a second laser light source for emitting laser light of a second wavelength different from the first wavelength;
    an optical detector for receiving scattered laser light from a measured part, the first laser light source, the second laser light source and the optical detector being disposed in the measuring apparatus on a same side of the measured part; and
    a controller configured to calculate a first value based on an output of the optical detector that is based on received scattered laser light of the first wavelength, calculate a second value based on an output of the optical detector that is based on received scattered laser light of the second wavelength, and measure oxygen saturation based on a ratio of the first value to the second value,
    wherein
    the optical detector includes a first optical detector and a second optical detector; and
    the first laser light source and the first optical detector are adjacent to each other along a linear axis, and the second laser light source and the second optical detector are adjacent to each other along the linear axis.

2. The measuring apparatus according to claim 1, wherein the laser light of the first wavelength is red light, and the laser light of the second wavelength is near infrared light.

3. The measuring apparatus according to claim 1, wherein the oxygen saturation is percutaneous arterial oxygen saturation, $SpO_2$.

4. The measuring apparatus according to claim 1, wherein a difference between an absorbance of oxyhemoglobin and an absorbance of reduced hemoglobin with respect to the first wavelength is greater than a difference between an absorbance of oxyhemoglobin and an absorbance of reduced hemoglobin with respect to the second wavelength.

5. The measuring apparatus according to claim 1,
wherein the scattered laser light of the first wavelength is the laser light of the first wavelength subjected to Doppler shift, and the scattered laser light of the second wavelength is the laser light of the second wavelength subjected to Doppler shift.

6. The measuring apparatus according to claim 1,
wherein the second value indicates a blood flow amount.

7. The measuring apparatus according to claim 5,
wherein the controller estimates a likelihood that a subject gets altitude sickness based on the oxygen saturation and a blood flow amount.

8. The measuring apparatus according to claim 1,
wherein the optical detector includes a first optical detector capable of detecting the scattered laser light of the first wavelength and a second optical detector capable of detecting the scattered laser light of the second wavelength.

9. The measuring apparatus according to claim 1,
wherein the optical detector is capable of detecting both the scattered laser light of the first wavelength and the scattered laser light of the second wavelength, and
the first laser light source and the second laser light source respectively emit at different timings.

10. The measuring apparatus according to claim 1, comprising at least any one of a cerebral blood flow meter capable of measuring a cerebral blood flow, a sphygmomanometer capable of measuring blood pressure, and a thermometer capable of measuring body temperature.

11. The measuring apparatus according to claim 1,
wherein a first value P1 is calculated from one of $P1 = K \cdot \int f \cdot P(f) df / (I \times I)$, $P1 = \int f \cdot P(f) df / (I \times I)$, and $P1 = \int f \cdot P(f) df$, where K represents a proportionality constant, I×I represents a mean square of an intensity of a received light signal, f represents a frequency, and P(f) represents a power spectrum of a beat signal.

12. The measuring apparatus according to claim 1,
wherein a second value P2 is calculated from one of $P2 = K \cdot \int f \cdot P(f) df / (I \times I)$, $P2 = \int f \cdot P(f) df / (I \times I)$, and $P2 = \int f \cdot P(f) df$, where K represents a proportionality constant, I×I represents a mean square of an intensity of a received light signal, f represents a frequency, and P(f) represents a power spectrum of a beat signal.

13. The measuring apparatus according to claim 1,
wherein the controller calculates the oxygen saturation from (the first value/the second value)×100.

14. The measuring apparatus according to claim 1,
wherein the controller calculates the oxygen saturation by performing predetermined weighting of a value of (first value/second value).

15. The measuring apparatus according to claim 1,
wherein the controller calculates the oxygen saturation by using a table for converting a value of (first value/second value) into the oxygen saturation.

16. The measuring apparatus according to claim 1,
wherein the first laser light source is configured to emit the laser light of the first wavelength to a superficial temporal artery and the second laser light source is configured to emit the laser light of the second wavelength to the superficial temporal artery.

17. The measuring apparatus according to claim 1,
wherein the first laser light source, the second laser light source and the optical detector are disposed at a same end of the measuring apparatus and proximate to each other.

18. The measuring apparatus according to claim 1,
wherein the first optical detector and the second laser light source are adjacent to each other.

19. The measuring apparatus according to claim 1,
wherein the first laser light source and the first optical detector are in contact with each other along a linear axis, and the second laser light source and the second optical detector are in contact with each other along the linear axis.

20. The measuring apparatus according to claim 1,
wherein the first optical detector and the second laser light source are adjacent to each other along the linear axis.

21. The measuring apparatus according to claim 1, further comprising:
at least one holding portion including the first laser light source, the second laser light source and the optical detector; and
a head band connected to the at least one holding portion and configured to position the at least one holding portion at the measured part.

22. The measuring apparatus according to claim 1, further comprising:
at least one holding portion including the first laser light source, the second laser light source and the optical detector;
a head band; and
a connecting portion which connects the headband to the at least one holding portion, and is configured as a damper to reduce vibration of the at least one holding portion.

* * * * *